(12) United States Patent
Holley

(10) Patent No.: US 7,992,770 B2
(45) Date of Patent: Aug. 9, 2011

(54) SPEC-TRAC

(76) Inventor: Charles Holley, Milford, PA (US)

( * ) Notice: Subject to any disclaimer, the term of this patent is extended or adjusted under 35 U.S.C. 154(b) by 874 days.

(21) Appl. No.: 11/155,460

(22) Filed: Jun. 18, 2005

(65) Prior Publication Data

US 2006/0283944 A1   Dec. 21, 2006

(51) Int. Cl.
*G06K 17/00*   (2006.01)
(52) U.S. Cl. .......................... 235/375; 235/385; 235/487
(58) Field of Classification Search .................. 235/375, 235/385, 435, 440, 459, 470, 487, 485
See application file for complete search history.

(56) References Cited

U.S. PATENT DOCUMENTS

| | | | | |
|---|---|---|---|---|
| 5,034,861 A * | 7/1991 | Sklenak et al. | ................. | 362/92 |
| 6,042,244 A * | 3/2000 | Witkoski | ....................... | 362/133 |
| 6,065,821 A * | 5/2000 | Anderson et al. | ............. | 312/408 |
| 6,193,152 B1 * | 2/2001 | Fernando et al. | ............. | 235/380 |
| 6,297,481 B1 * | 10/2001 | Gordon | ......................... | 219/406 |
| 6,729,144 B1 * | 5/2004 | Kupferman | ....................... | 62/3.6 |
| 6,813,896 B1 * | 11/2004 | Janke et al. | ..................... | 62/126 |
| 6,817,522 B2 * | 11/2004 | Brignone et al. | ............. | 235/385 |
| 7,163,305 B2 * | 1/2007 | Bienick | ........................... | 362/92 |
| 7,369,919 B2 * | 5/2008 | Vonk et al. | ..................... | 700/236 |
| 7,688,207 B2 * | 3/2010 | Fritchie et al. | ............. | 340/572.1 |
| 2002/0067270 A1 * | 6/2002 | Yarin et al. | ................. | 340/573.1 |
| 2003/0069699 A1 * | 4/2003 | Ekins et al. | ..................... | 702/19 |
| 2004/0113786 A1 * | 6/2004 | Maloney | .................... | 340/568.1 |
| 2005/0098626 A1 * | 5/2005 | Jordan et al. | .................. | 235/381 |
| 2005/0276728 A1 * | 12/2005 | Muller-Cohn et al. | ........ | 422/102 |
| 2006/0110373 A1 * | 5/2006 | Regnier et al. | ............... | 424/93.7 |

* cited by examiner

*Primary Examiner* — Edwyn Labaze

(57) ABSTRACT

Spec-Trac is a computerized specimen rack storage system. The main focal point of the invention is the computerized storage racks that allow the user to scan barcode \ labeled specimens and place them in the rack as directed by the computer, using LED's, proximity switches, and computer technology In addition, the rack's are stored in refrigeration/ freezer units that connect the racks to a network, and allow the racks to synchronize its database with the main storage server, using standard network wired or wireless technology. Specimen retrieval can occur at the computerized rack, individual storage units, or the main database server.

4 Claims, 6 Drawing Sheets

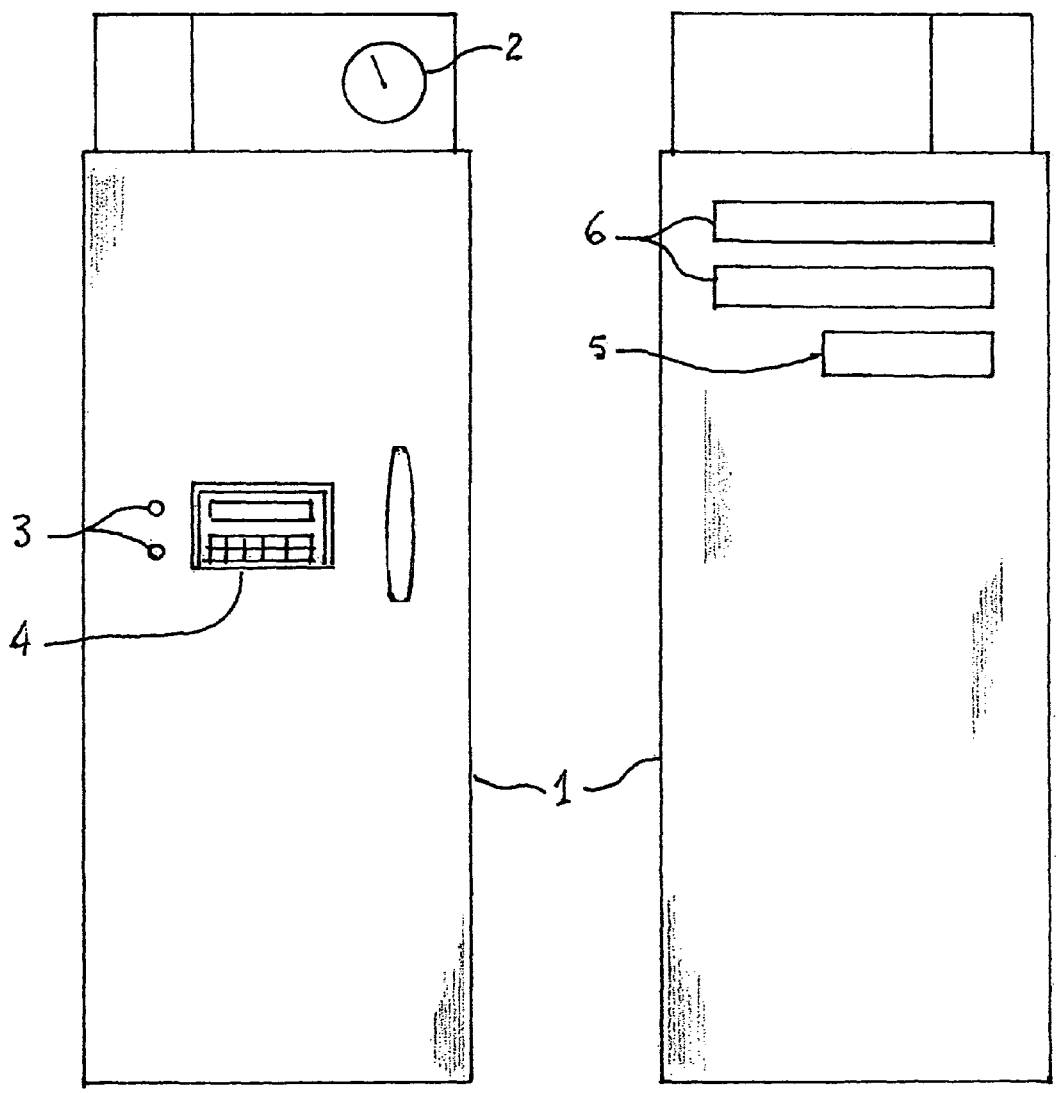

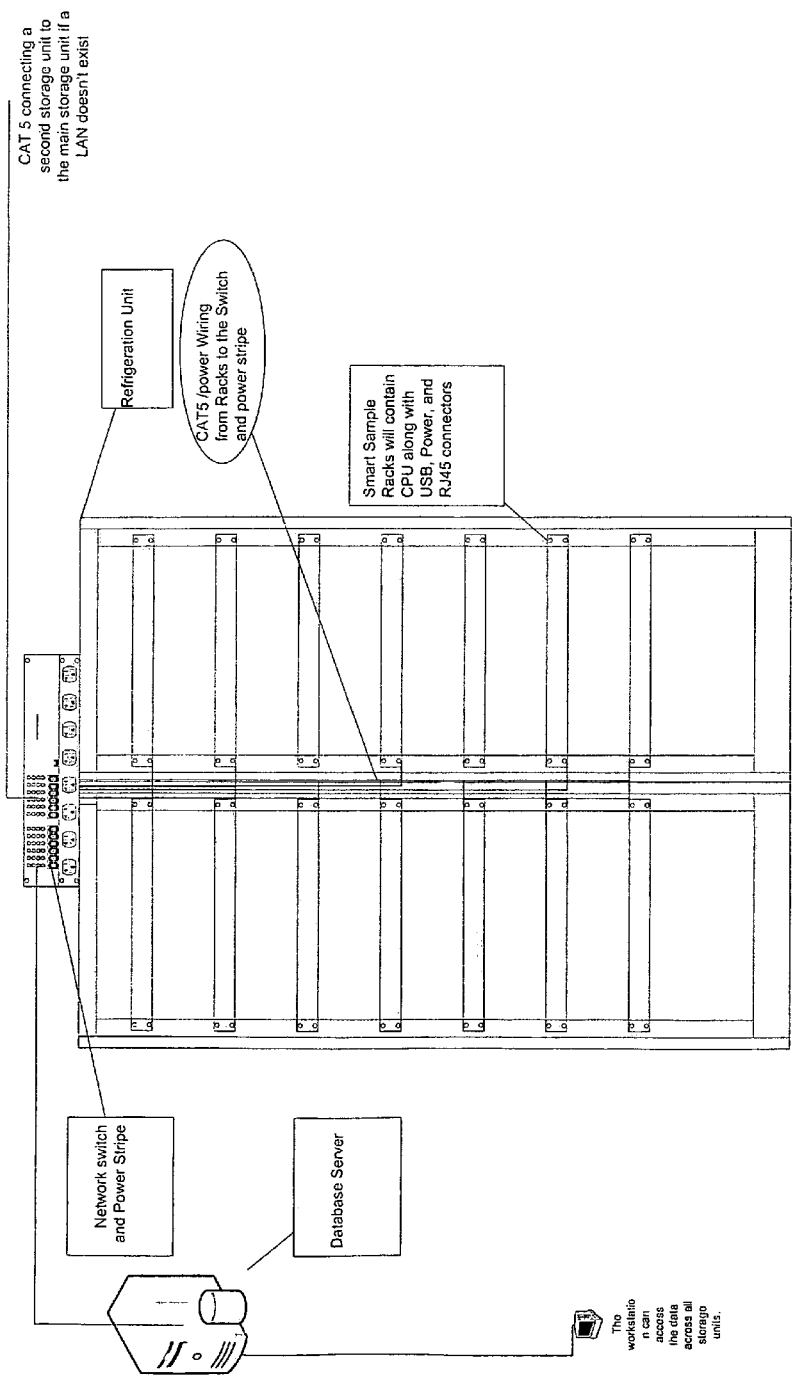

SPEC-TRAC

BACKGROUND OF INVENTION

Spec-trac is designed to assist laboratory professionals, most commonly in a hospital setting, electronically track bar coded specimens in a decentralized/centralized fashion.

The Current state of the technology in a hospital setting remains manual. Today bar coded specimens are commonly placed in racks, using manual numbering schemes that correspond to the last digit in the barcode.
This lends itself to wasting rack space, lost specimens due to human error, and inefficient specimen retrieval.

SUMMARY OF THE INVENTION

Spec-trac is a barcode identified specimen tracking system, designed to allow decentralized specimen placement and retrieval. This system can be used for a variety of specimens, the only requirement is that the specimen is bar coded, and readable via scanner.

Through the merging of existing technologies, Spec-Trac will allow laboratory professionals to place specimens into racks scanned by a bar code laser scanner and retrieved via a keypad/keyboard. In addition, the information stored in the decentralized racks concerning each racks' inventory can be downloaded when the rack is returned to a storage unit, and transferred to a main database server via a wireless or wired technology.

Spec-Trac consists of the following major functional parts: refrigeration/freezer units with network switches, computerized storage racks, main database server, wired or wireless interfaces to the computerized storage racks, laser barcode readers, and computerized rack keypads.

DESCRIPTION OF THE SEVERAL VIEWS OF THE DRAWING

FIG. 1 is a front view of the storage unit with it's laser reader, keypad, display, and QA graph.

FIG. 2 is a rear view of the storage unit with it's Network switch, and Power strip on the main storage unit.

FIG. 7 is a display of the main server it's connection to the other major components (PC based technology)

DETAIL DESCRIPTION OF THE INVENTION

Figure 3:
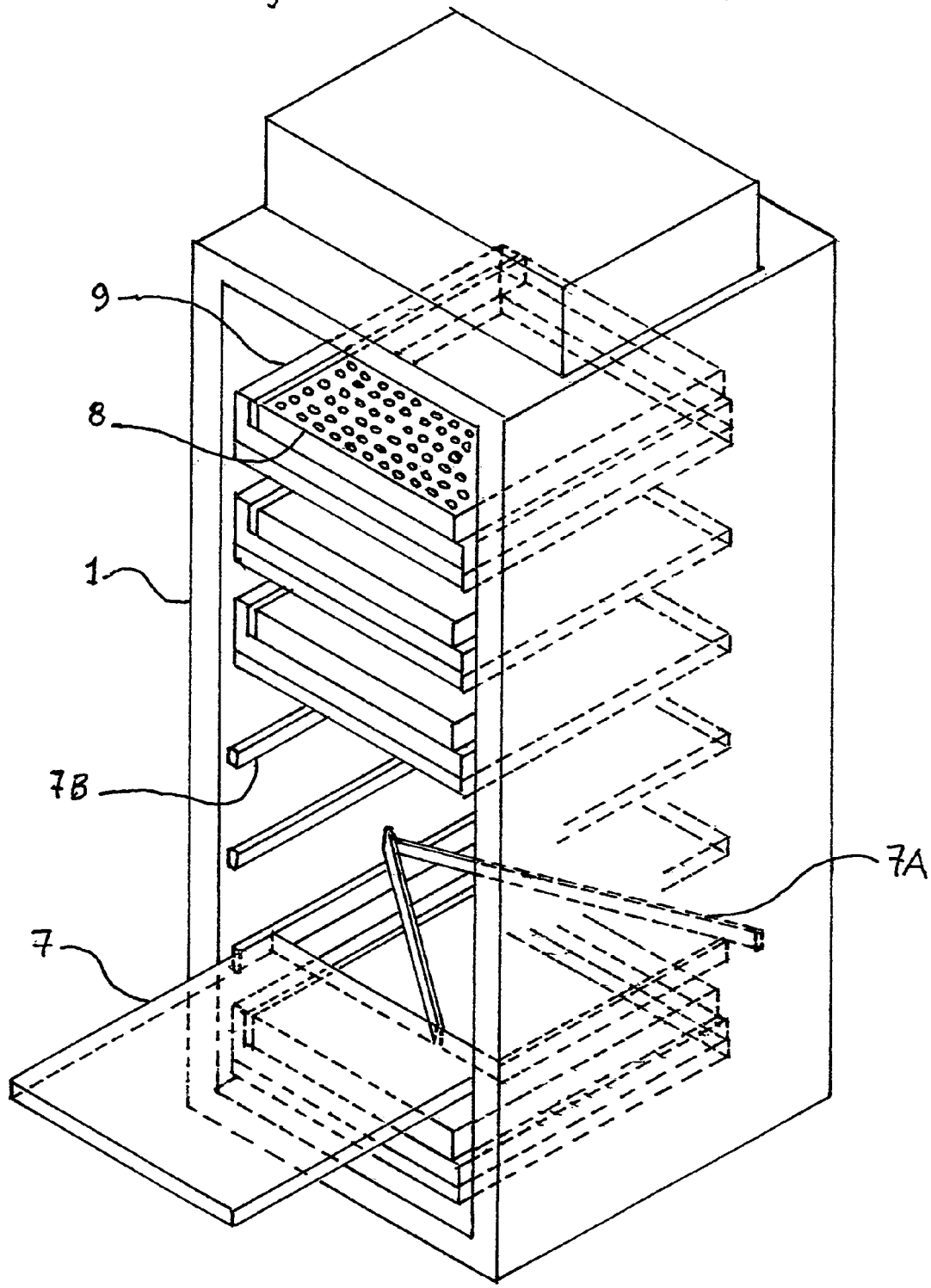
FIG. 3 is a front view of the storage unit with the doors removed to display the shelves for the computerized storage racks and cable management.

Main refrigeration/freezer units will house the computerized storage racks that contain its local inventory, and provide a means to synchronize the local inventory storage unit by connecting each computerized storage rack to the main database server via a network switch and network cabling.
This provides redundant paths to access specimen data. Each refrigeration/freezer unit will contain a keypad, and scanner on the door, to access specimens located within it's local unit. When a rack or racks are removed from a storage unit, the data on the rack(s) will be deleted from the main database server as soon as the specimens are dumped and connectivity is reestablished. In addition, multiple refrigeration/freezer units can be connected via a local area network, wired or wireless. In the absence of a local area network the units can be linked via CAT5 locally installed network switches, within each refrigerator/freezer unit, that in turn will connect each unit to the primary database server.

Reference is made to FIG. 1, wherein Item 1 illustrates the front panel of the primary storage unit. Item 2 illustrates the Quality Assurance graph associated with all laboratories refrigeration. Bear in mind the primary storage unit can have double or triple door units. These multiple units are only limited by current refrigeration standards. Item 3 indicate the USB connection used or laser reader or backup keypad in case the primary keypad fails.

FIG. 2 illustrates the backside of the Primary storage unit. Item 5 represents the power strip using current technology to provide power to each of the computerized specimen racks. Item 6 indicates the placement of a network switch, which is used to provide connectivity between the computerized specimen racks and the primary database server.

The computerized storage racks, have the following features, (side) external power supply plug-in, RJ45 connection for networking, embedded wireless network card, multiple USB connections for an external laser reader, an external keypad, LED's and Proximity switches. Each rack will have illumination for specimen retrieval
and placement. Each rack will contain current computer technology that allows local storage of all inventory information, and a network (RJ45 connection) or wireless interface back to the main database server.

The user will place specimens into the rack via the laser reader. When placing specimens the user will read the barcode, and the next available slot LED will illuminate. If multiple samples exist with the same tracking number, they can be placed by reading each subsequent specimen. To retrieve a specimen the user will enter at least the last five digits of the tracking number. If specimens exist, the corresponding LED(s) will light in a blinking fashion. At the beginning of each use the rack can be emptied, this will blank out the local storage when the proximity switches reset. The local database within the rack will synchronize with the main database server once connectivity is reestablished.

FIG. 3 provides a three dimensional view of the inside of the primary or secondary storage unit minus the cabling and front door. Item 1 is the Primary storage/refrigeration unit, which can be either a refrigerator or freezer unit. Item 7A represent the cabling arm used for cable management within a storage unit. The power and CAT 5 cabling will be run along these arms to the support shelf (Item 7). Item 7B represents the rails used by Item 7 to allow the shelves to pull out easily. Item 8 shows a computerized specimen rack residing on one of the pull out shelves in the primary storage unit. Item 9 represents the control device enclosure that houses the printed circuit boards for relaying and computer components.

Figure 4:
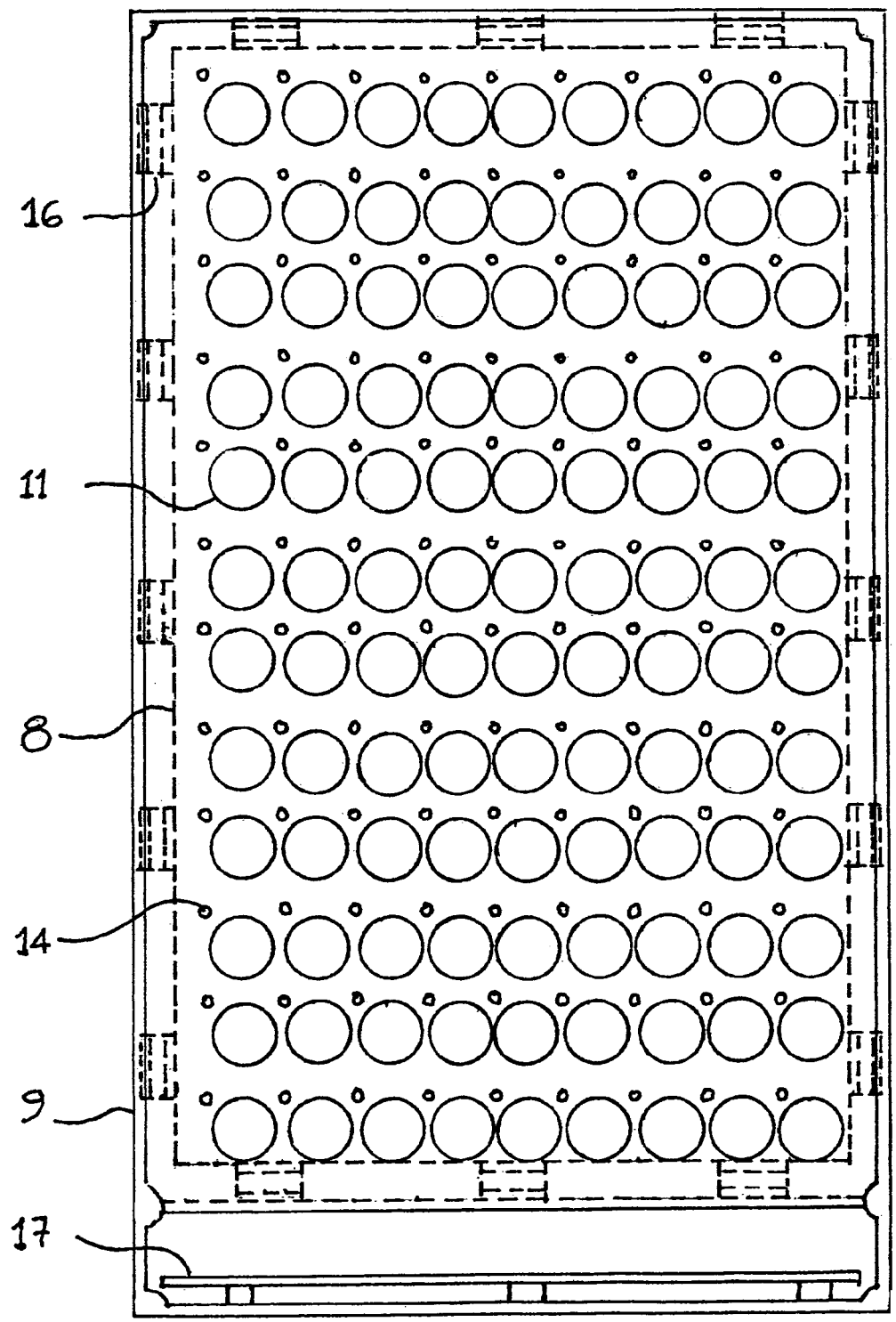
FIG. 4 is a bottom view of the computerized storage rack, displaying the proximity sensor, LED locations, and printed circuit boards.

FIG. 4 shows the bottom view of the computerized specimen rack. Item 11 shows the proximity sensors embedded under each rack slot. Item 13 indicates the LED lamps adjacent to the proximity sensors used for slot illumination as a visual queue to the clinician.

Figure 5:
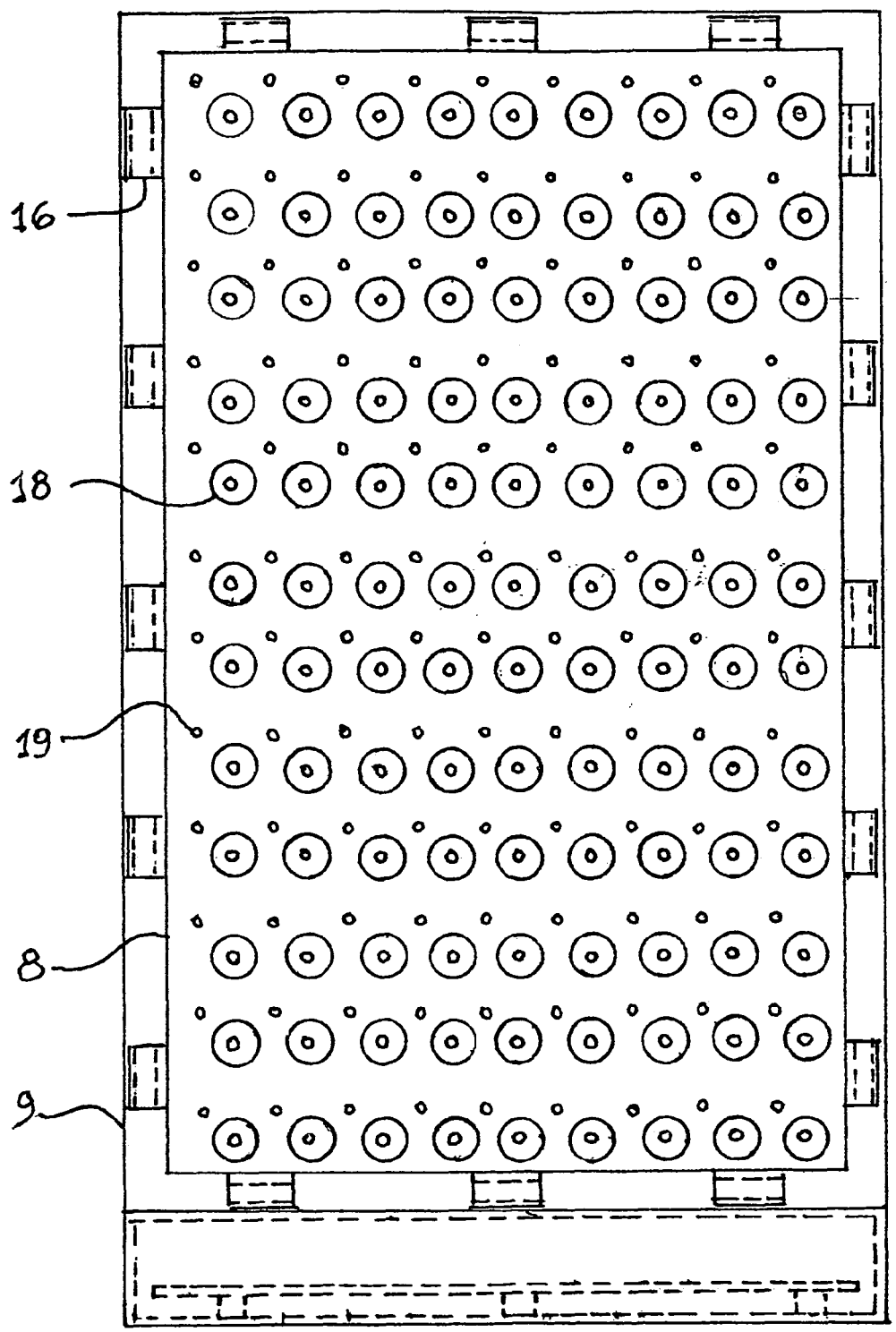
FIG. 5 is a top view of the computerized storage racks displaying the specimen slots, and LED displays.

FIG. 5 shows a top view of the computerized specimen rack. Item 8 indicates the general dimension of the computerized rack. Item 9 indicates the control device enclosure which contains the proximity sensors, LED's in serial wiring, relay boards, and computer. Item 11 indicates the proximity sensors within each slot of the rack. Item 16 indicates the top of the racks retaining clips. This allows the top of the rack to be removed for cleaning. Item 17 indicates the compartment for printed circuit board for relaying and computer components.

Figure 6:
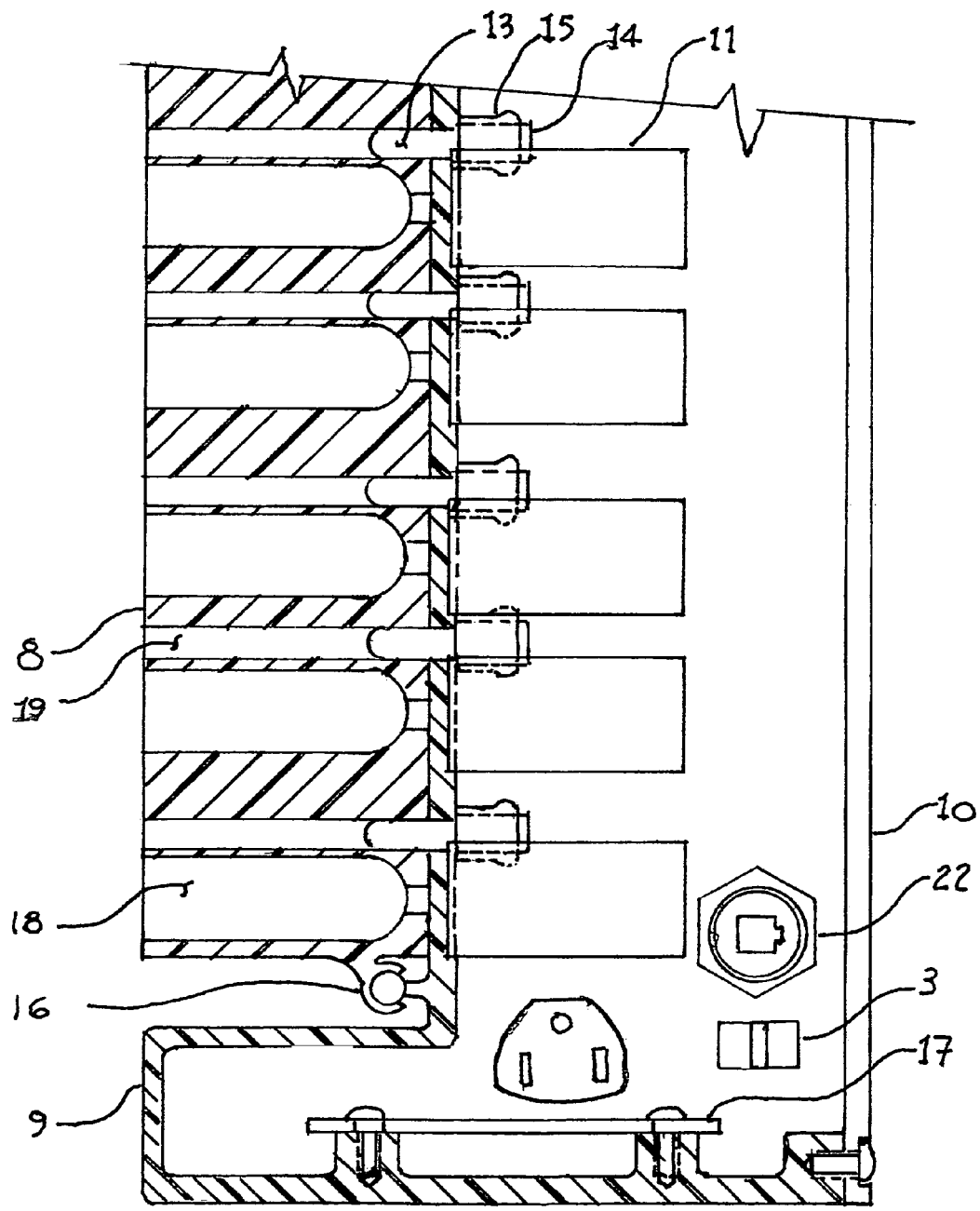
FIG. 6 is a cross section view of the rack, that outlines the LED's, proximity sensors, CAT 5 connection, USB connection, and computer compartment/relay board enclosure.

FIG. 6 shows a cross section of the computerized specimen rack. Item 3 shows the USB connections used for the laser reader and keypad. Item 8 indicates the general computerized specimen rack. Item 9 shows the compartment used for printed circuit boards for relaying, and computer components. Item 10 is the bottom cover for the electronic components of the computerized specimen rack which is water and airtight. Item 11 show a cross sectional view of the proximity sensor that lies at the bottom of each slot in the rack. Item 13 shows the cross section of the LED/signal lamps used to provide a visual indicator to the user, which slot to place or remove a specimen from. Item 19 is the illumination cavity used to convey the LED light to the top of the rack, which in turn provides the visual queue to the clinician for next available slot for specimen placement or specimen retrieval. Item 14 is a socket that holds the signal lamp. Item 15 is a signal lamp retainer. Item 16 is the top of the computerized specimen rack retaining clip in cross section. Item 17 show one of the circuit boards attached within the control device enclosure. Item 18 is the specimen slot in the rack in cross section.

The main database server can be connected to each of the storage units via wired network switches, and or wireless interface via wireless access points. The purpose of the main server is to retrieve specimens across multiple refrigeration/freezer units. The server removes a single point of data loss, and performs other specimen management functionality. Those functions being, but not limited to, assigning racks/storage units to individual areas in a laboratory (Chemistry, Hematology, etc.). Each rack, and each refrigeration unit will have a unique software identifier that is used to tie the racks, and units to individual laboratory sections. The server will also be used to push firmware updates to racks, and storage units.

FIG. 7 shows a schematic view of the major network functional component involved. Item 20 shows the Main Database Server used as the primary database for computerized rack inventory. This also provides a redundant inventory, because, in addition to the primary database, each rack will contain it's local storage information. Item 21 shows a computer at a workstation that will run a software client sample to allow communication back to the primary database. In addition, but not displayed, the computerized storage racks are also located at the workstation, and as described above, can have real time connectivity to the primary database for data synchronization, once placed back in the primary storage unit at the end of it's active use. Item 22 show the CAT 5 network connectivity between the major components. This connectivity is not limited to a wired configuration. All major components can use wireless technology if the organization in question can accommodate it.

What is claimed is:

1. Spec-Trac specimen storage and retrieval system for small to medium size laboratories comprising: computerized laboratory specimen storage racks connecting to a network, wherein the computerized laboratory specimen storage racks communicate back to a main database server using standard wired or wireless networking technology; at least one or more refrigeration/freezer storage units to store said computerized laboratory specimen storage racks while not being actively used, utilizing CAT 5 and RJ45 connections back to an on-board switch that connects to a Local Area Network using standard wired, or wireless network technology; a main laboratory specimen database storage server utilizing standard computing technology (wired or wireless) to communicate and store specimen location information within each specimen racks; for future retrieval of said laboratory specimen(s), and wherein each storage unit will contain an adequate power strip to power each computerized rack stored in the laboratory specimen refrigeration/freezer units.

2. Networked, computerized specimen racks will allow users to readily store barcoded specimens wherein: each slot in the specimen rack will have a corresponding LED and proximity switch; the LED's will be used as an end user interface, to identify a next available slot, to identify a slot containing a specimen an end user is looking for, wherein, a barcode reader connected to the rack using a standard USB connector, will scan a barcode, software will light the LED corresponding to a next available slot in the rack, which directs the user to place the specimen in the illuminated slot, a proximity switch will allow software to determine slot availability, an on board computer will then allow software to store the barcode number and slot position; wherein, if the rack is connected to a laboratory network at a specimen test station, via an RJ45 connection or wireless interface, it will communicate that information to a main database server real-time, or, if not connected to a laboratory network, software installed on the on board computer will synchronize with a main laboratory database server, upon returning a rack to a storage unit, (refrigerator or freezer) and connected via an RJ45 network connection; said racks utilizing software will keep track of unique internal slot identification numbers, such that each specimen storage rack utilizing standard computer client server technology hardware and software, will have a unique IP address, and each rack will be assigned to a specific organization section (i.e. chemistry, or hematology department) wherein said racks will be assigned to specific refrigerated storage units, but not specific shelves within the storage unit.

3. Spec-Trac, utilizing software installed on the onboard computer, will allow users to quickly retrieve specimens from a refrigerated storage rack, via multiple access points When a storage rack is actively being used to store new specimens in a specimen test station, the user will be able to identify subject specimens utilizing a keypad attached to the rack via a standard USB connector, wherein, by keying in a partial or whole barcode number, software will light the storage slot corresponding to the number entered, and, when removing older laboratory samples, the user can access an accession number, using a software client that communicates with a main laboratory database server, via a standard PC, the user can enter a partial or whole barcode number at a specimen test station, the software will light corresponding LED(s) across multiple specimen racks, in multiple storage units (refrigerators/freezers).

4. Spec-Trac will allow for efficient database storage and specimen maintenance, wherein; expired samples are removed from a specimen storage rack, and the rack is returned to a storage (refrigerator/freezer) unit, for use to store new samples; proximity switch(es) will reset the specimen storage slots to an open or available status and purge barcodes associated with the corresponding specimen storage slots, and when a specimen storage rack is either connected to an LAN using an RJ45 connection or returned to the storage unit (refrigerator) at the end of use, said specimen storage rack will synchronize with a main laboratory database server; each rack containing a local database, and a main database server will contain a duplicate copy of that data for redundancy; alternately, when a wireless interface card is used, a specimen storage rack will update the main database server real-time when a specimen is removed or added, if a specimen(s) is retrieved from a specimen storage rack, and needs to be returned, the user must scan the specimen again to return it to a specimen storage rack.

* * * * *